United States Patent [19]

Strader et al.

[11] Patent Number: 5,336,595
[45] Date of Patent: Aug. 9, 1994

[54] METHOD OF USING HUMAN NEUROKININ-1 RECEPTOR SHORT FORM

[75] Inventors: Catherine D. Strader, Verona; Tung M. Fong, Somerset, both of N.J.

[73] Assignee: Merck & Co., Inc., Rahway, N.J.

[21] Appl. No.: 701,935

[22] Filed: May 17, 1991

[51] Int. Cl.$^5$ .............................................. C12Q 1/68
[52] U.S. Cl. ...................... 435/6; 435/7.21; 435/29; 435/320.1; 436/503; 436/504
[58] Field of Search ............... 435/6, 7.21, 320.1, 435/29, 968; 436/503, 504

[56] References Cited

FOREIGN PATENT DOCUMENTS

WO92/16547 11/1992 PCT Int'l Appl. .

OTHER PUBLICATIONS

Yokota et al. *J. Biol. Chem.* 264(30): 17649–17652 (1989).
Dijkema et al. *The Embo Journal* 4(3): 761–767(1985).
Torrens, et al. *J. Neurochem.* 52: 1913–1918(1989).
Sambrook et al. in *Molecular Cloning* pp. 16.15–16.22, 8.46–8.48, 16.69–16.72 (1989).
Invitrogen catalogue, pp. 31, 50, (1990).
Hopkins, et al., "Isolation and Characterization of the Human Lung NK-1 Receptor cDNA", *Biochem & Biophys. Res. Commun.*, 180(2), 1110-7 (1991).
Takeda, et al., "Molecular Cloning, Structural Characterization and Functional Expression of the Human . . .", *Biochem & Biophys. Res. Commun.*, 179(3), 1232–40 (1991).
Gerard, et al., "Human Substance P Receptor (NK-1): Organization of the Gene, Chromosome Localization . . . ", *Biochem.*, 30(44), 10640–46 (1991).
*Patent Abstracts of Japan*, "Substance P Receptor and Gene Thereof", 015(341), Aug. 29, 1991 (JP3133998).
Cascieri, et al., *J. Biol. Chem.*, 258, 5158–5164 (1983).
Lundblad, et al. *Acta Otolaryngol*, 96, 485–493 (1983).
Payan, et al., *J. Immunol.*, 131, 1613–15 (1983).
Masu, et al., *Nature*, 329, 836–838 (1987).
Sasai, et al., *Biochem. Biophys. Res. Commun.*, 165, 695–702 (1989).
Shigemoto, et al., *J. Biol. Chem.*, 265, 623–628 (1990).
Gerard, et al. (I), *J. Biol. Chem.*, 265, 20455–62 (1990).
Hershey, et al., *Science*, 247, 958–962 (1990).
McLean, et al, *Science*, 251, 437–439 (1991).
Gerard, et al. (II), *FASEB J.*, 5(5) 4647 (Mar. 15, 1991).
U.S. application Ser. No. 691,197, filed Apr. 25, 1991, Fong et al.
U.S. application Ser. No. 691,198, filed Apr. 25, 1991 Fong et al.
U.S. application Ser. No. 691,200, filed Apr. 25, 1991, Fong et al.
U.S. application Ser. No. 701,930, filed May 17, 1991, Strader et al.
U.S. application Ser. No. 701,937, filed May 17, 1991, Strader et al.

*Primary Examiner*—Esther L. Kepplinger
*Assistant Examiner*—Donna C. Wortman
*Attorney, Agent, or Firm*—C. M. Caruso; J. E. Thies

[57] ABSTRACT

A novel recombinant human neurokinin-1 receptor short form (hereinafter identified as human NK1R sF) is disclosed which has been prepared by polymerase chain reaction techniques. Also disclosed is the complete sequence of human NK1R sF complementary DNA; expression systems, including a CHO (Chinese hamster ovarian cell line) stable expression system; and an assay using the CHO expression system.

NK1R sF, can be used in an assay to identify and evaluate entities that bind substance P receptor or NK1R sF. The assay can also be used in conjunction with diagnosis and therapy to determine the body fluid concentration of substance P antagonists in arthritis patients.

4 Claims, 7 Drawing Sheets

```
              10                              20
Met Asp Asn Val Leu Pro Val Asp Ser Asp Leu Ser Pro Asn Ile Ser Thr Asn Thr Ser
              30                              40
Glu Pro Asn Gln Phe Val Gln Pro Ala Trp Gln Ile Val Leu Trp Ala Ala Ala Tyr Thr
              50                              60
Val Ile Val Val Thr Ser Val Val Gly Asn Val Val Val Met Trp Ile Ile Leu Ala His
              70                              80
Lys Arg Met Arg Thr Val Thr Asn Tyr Phe Leu Val Asn Leu Ala Phe Ala Glu Ala Ser
              90                              100
Met Ala Ala Phe Asn Thr Val Val Asn Phe Thr Tyr Ala Val His Asn Glu Trp Tyr Tyr
              110                             120
Gly Leu Phe Tyr Cys Lys Phe His Asn Phe Phe Pro Ile Ala Ala Val Phe Ala Ser Ile
              130                             140
Tyr Ser Met Thr Ala Val Ala Phe Asp Arg Tyr Met Ala Ile Ile His Pro Leu Gln Pro
              150                             160
Arg Leu Ser Ala Thr Ala Thr Lys Val Val Ile Cys Val Ile Trp Val Leu Ala Leu Leu

FIG. 1A
```

```
                                                        180
Leu Ala Phe Pro Gln Gly Tyr Tyr Ser Thr Thr Glu Thr Met Pro Ser Arg Val Val Cys
                                                        200
Met Ile Glu Trp Pro Glu His Pro Asn Lys Ile Tyr Glu Lys Val Tyr His Ile Cys Val
                                                        220
Thr Val Leu Ile Tyr Phe Leu Pro Leu Val Ile Gly Tyr Ala Tyr Thr Val Val Gly
                                                        240
Ile Thr Leu Trp Ala Ser Glu Ile Pro Gly Asp Ser Ser Asp Arg Tyr His Glu Gln Val
                                                        260
Ser Ala Lys Arg Lys Val Val Lys Met Met Ile Val Val Val Cys Thr Phe Ala Ile Cys
                                                        280
Trp Leu Pro Phe His Ile Phe Phe Leu Leu Pro Tyr Ile Asn Pro Asp Leu Tyr Leu Lys
                                                        300
Lys Phe Ile Gln Gln Val Tyr Leu Ala Ile Met Trp Leu Ala Met Ser Ser Thr Met Tyr
                     310
Asn Pro Ile Ile Tyr Cys Cys Leu Asn Asp Arg
```

FIG. 1B

```
 10          20          30          40          50          60          70
GAAAAAGCCT TCCACCCTCC TGTCTGGCTT TAGAAGGACC CTGAGCCCCA GGCGCCACGA CAGGACTCTG 80          90         100         110         120         130         140
CTGCAGAGGG GGGTTGTGTA CAGATAGTAG GGCTTTACCG CCTAGCTTCG AAATGGATAA CGTCCTCCCG 150         160         170         180         190         200         210
GTGGACTCAG ACCTCTCCCC AAACATCTCC ACTAACACCT CGGAACCCAA TCAGTTCGTG CAACCAGCCT 220         230         240         250         260         270         280
GGCAAATTGT CCTTTGGGCA GCTGCCTACA CGGTCATTGT GGTGACCTCT GTGGTGGGCA ACGTGGTAGT 290         300         310         320         330         340         350
GATGTGGATC ATCTTAGCCC ACAAAAGAAT GAGGACAGTG ACGAACTATT TTCTGGTGAA CCTGGCCTTC 360         370         380         390         400         410         420
GCGGAGGCCT CCATGGCTCT ATTCAATACA GTGGTGAACT TCACCTATGC TGTCCACAAC GAATGGTACT 430         440         450         460         470         480         490
ACGGCCTGTT CTACTGCAAG TTCCACAACT TCTTCCCCAT CGCCGCTGTC TTCGCCAGTA TCTACTCCAT
```

FIG. 2A

```
         500        510        520        530        540        550        560
GACGGGCTGTG GCCTTTGATA GGTACATGGC CATCATACAT CCCCTCCAGC CCCGGCTGTC AGCCACAGCC 570        580        590        600        610        620        630
ACCAAAGTGG TCATCTGTGT CATCTGGGTC CTGGCTCTCC TGCTGGCCTT CCCCAGGGGC TACTACTCAA 640        650        660        670        680        690        700
CCACAGAGAC CATGCCCCAG AGAGTCGTGT GCATGATCGA ATGGCCAGAG CATCCGAACA AGATTTATGA 710        720        730        740        750        760        770
GAAAGTGTAC CACATCTGTG TGACTGTGCT GATCTACTTC CTCCCCCTGC TGGTGATTGG CTATGCATAC 780        790        800        810        820        830        840
ACCGTAGTGG GAATCACACT ATGGGCCAGT GAGATCCCCG GGGACTCCTC TGACCGCTAC CACGAGCAAG 850        860        870        880        890        900        910
TCTCTGCCAA GCGCAAGGTG GTCAAAATGA TGATTGTCGT GGTGTGCACC TTCGCCATCT GCTGGCTGCC 920        930        940        950        960        970        980
CTTCCACATC TTCTTCCTCC TGCCCTACAT CAACCCAGAT CTCTACCTGA AGAAGTTTAT CCAGCAGGTC

FIG. 2B
```

```
      990        1000       1010       1020       1030       1040       1050
TACCTGGCCA TCATGTGGCT GGCCATGAGC TCCACCATGT ACAACCCCAT CATCTACTGC TGCCTCAATG 1060       1070       1080       1090       1100       1110       1120
ACAGGTGAGG ATCCCAACCC CATGAGCTCT CCAGGGGCCA CAAGACCATC TACATACACA GTGGCCAAGC 1130       1140       1150       1160       1170       1180       1190
GGCATCCCTAA ATGAGTAAAC CCAGCTGTGA GACAAGAGGG ACAAGTGGGG ACTGCAGCTA ACTTATCATC 1200       1210       1220       1230       1240       1250       1260
ACACAACTCA GCCTGGCTGA TTATCACCAT CCAGGAATGG GAGCCCGGAG TAGACTGATT TTCTTTTTTT

CTTTTCCAC
```

FIG. 2C

METHOD OF USING HUMAN NEUROKININ-1 RECEPTOR SHORT FORM

BACKGROUND OF THE INVENTION

The present invention concerns a novel cloned human neurokinin-1 receptor short form (hereinafter identified as human NK1R sF) and recombinant human NK1R sF.

J. Yokota, et al., J. Biol. Chem., 264:17649 (1989) have reported cloned rat neurokinin-1 receptor. N.P. Gerard, et al., J. Biol. Chem., 265:20455 (1990), have reported human neurokinin-2 receptor. Cloned rat and bovine neurokinin-2 receptor have likewise been reported. See respectively, Y. Sasi, and S. Nakanishi, Biochem Biophys. Res. Comm., 165:695 (1989), and Y. Masu, et al., Nature 329:836 (1987). Cloned rat neurokinin-3 receptor has also been reported by R. Shigemoto, et al., J. Biol. Chem., 265:623 (1990).

The above references, however, neither disclose or suggest the instant invention.

Substance P is a naturally occuring undecapeptide belonging to the tachykinin family of peptides. Substance P is a pharmacologically-active neuropeptide that is produced in mammals. Its characteristic amino acid sequence is illustrated in U.S. Pat. No. 4,680,283. As is well known in the art substance P and other tachykinins have been implicated in the pathophysiology of numerous diseases. Substance P has been shown to be involved in the transmission of pain or migraine (see B. E. B. Sandberg et al., *Journal of Medicinal Chemistry*, Vol. 25, p. 1009 (1982)), as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis and Crohn's disease, etc. (see D. Regoli in "Trends in Cluster Headache," edited by F. Sicuteri et al., Elsevier Scientific Publishers, Amsterdam, 1987, pp. 85-95).

The instant invention also concerns an assay protocol which can be used to determine the activity in body fluids of substances that bind human NK1R or NK1R sF; these include substance P The assay can also be used for identifying and evaluating substances that bind NK1R or NK1R sF. Thus, the assay can be used to identify substance P antagonists and evaluate their binding affinity. Other methods includes that described by M. A. Cascieri, et al., J. Biol. Chem., 258-5158 (1983). By use of such methods, substance P antagonists have been identified. See, for example, R. M. Snider, et al., Science, 251:435 (Jan. 1991) and S. McLean, et al., Science, 251:437 (Jan. 1991). See also WO90/05525 which published May 31, 1990, which is hereby incorporated by reference. Methods to date have proven inferior, in part, for failure of the animal receptor (animal NK1R, NK2R or NK3R) activity to accurately reflect that of human neurokinin-1 receptor. Furthermore, prior to this disclosure human NK1R has not been available in a purified form or in substantial isolation from NK2R and/or NK3R. Use of such neurokinin receptor sources cannot accurately depict the affinity for a human NK1R, and in particular, NK1R sF.

BRIEF DESCRIPTION OF THE DRAWINGS

FIG. 1: Full length amino acid sequence of human neurokinin-1 receptor short form.

FIG. 2: Full length nucleotide sequence of the cloned human neurokinin-1 receptor short form complementary DNA.

SUMMARY OF THE INVENTION

Figure 3:
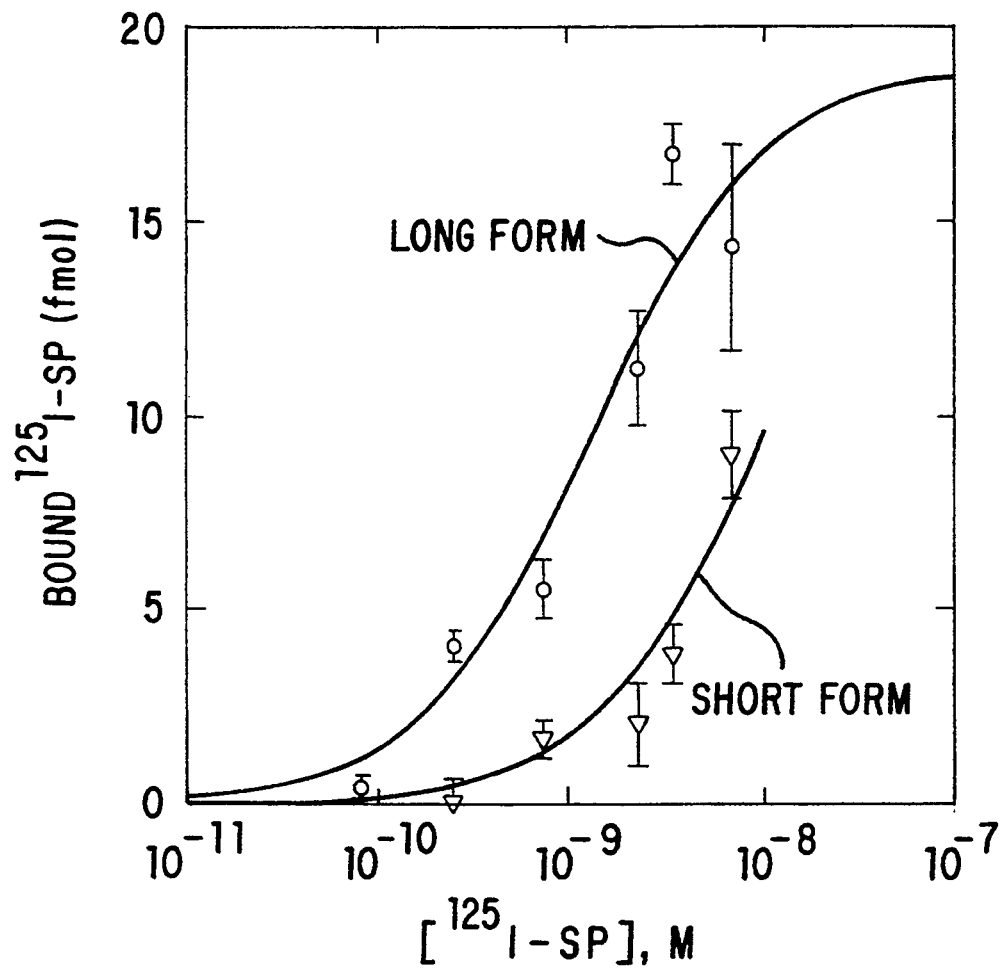
FIG. 3: Binding affinity of neurokinin-1 receptor long (NK1R) and short forms (NK1RSF) for substance P (SP) in COS assay.

A novel recombinant human neurokinin-1 receptor short form (hereinafter identified as human NK1R sF) is disclosed which has been prepared by polymerase chain reaction techniques. Also disclosed is the complete sequence of human NK1R sF complementary DNA; expression systems, including a CHO (Chinese hamster ovarian cell line) stable expression system; and an assay using the CHO expression system.

NK1R sF, can be used in an assay to identify and evaluate entities that bind substance P receptor or NK1R sF. The assay can also be used in conjunction with diagnosis and therapy to determine the body fluid concentration of substance P antagonists in arthritis patients.

DETAILED DESCRIPTION OF THE INVENTION

One embodiment of the invention concerns human neurokinin-1 receptor short form, said receptor being free of other human receptor proteins.

In one class this embodiment concerns human neurokinin-1 receptor short form, said receptor being free of other human proteins.

Within this class, this embodiment concerns human neurokinin-1 receptor short form from human cells such as glioblastoma, said receptor being free of other human proteins.

In a second class, this embodiment concerns a protein comprising the 311 amino acid sequence depicted in FIG. 1, said protein being free of other human receptor proteins.

Within the second class this embodiment concerns a protein consisting of the 311 amino acid sequence as shown in FIG. 1.

The first embodiment also concerns a pharmaceutical composition for inhibiting the binding of substance P to cellular neurokinin-1 receptor or a cellular neurokinin-1 receptor short form, said composition comprising an effective amount of neurokinin-1 receptor short form.

The first embodiment also concerns a method of inhibiting the binding of substance P to cellular human neurokinin-1 receptor or a cellular neurokinin-1 receptor short form, in a patient in need of such inhibition, comprising: administration of an effective amount of human neurokinin-1 receptor short form.

The use of such pharmaceutical compositions and methods for antagonising the binding of substance P to in vivo neurokinin-1 receptor is disclosed in, for example, R. M. Snider, et al., *Science*, 251:435 (Jan. 1991); S. McLean, et al., *Science*, 251:437 (Jan. 1991); and *PCT Patent application* WO90/05525 which published May 31, 1990. The administration of an effective amount of human neurokinin-1 receptor short form may be conducted utilizing essentially the same procedure.

A second embodiment concerns a DNA sequence encoding human neurokinin receptor short form complementary DNA, said DNA, said sequence being free of other human DNA sequences.

As will be appreciated by those of skill in the art, there is a substantial amount of redundancy in the set of codons which translate specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenerate variation. Also included are mutations (exchange of individual amino acids) which one of skill in the art would expect to have no effect on functionality, such as valine for leucine, arginine for lysine and asparagine for glutamine.

One class of the second embodiment of the invention concerns the nucleotide sequence of complementary DNA, beginning with nucleotide 123 and ending with nucleotide 1055 as shown in FIG. 2.

Within this class of the second embodiment is the DNA sequence (SEQ ID NO:1:) that further comprises:

```
        10          20          30          40          50          60          70
GAAAAAGCCT  TCCACCCTCC  TGTCTGGCTT  TAGAAGGACC  CTGAGCCCCA  GGCGCCACGA  CAGGACTCTG 80          90         100         110         120  122
CTGCAGAGGG  GGGTTGTGTA  CAGATAGTAG  GGCCTTTACCG CCTAGCTTCG  AA
``` or a degenerate variation thereof.

The second embodiment of the invention concerns the partial nucleotide sequence of complementary DNA, as shown in FIG. 2 or a degenerate variation thereof.

A third embodiment of this invention concerns systems for expressing human neurokinin-1 receptor short form.

One class of this third embodiment of the invention comprises:

A plasmid which comprises:
(a) a mammalian expression vector, such as pRcCMV, and
(b) a base sequence encoding human neurokinin-1 receptor short form protein.

Within this class of the third embodiment the neurokinin-1 receptor short form comprises the nucleotide sequence of complementary DNA, beginning with nucleotide 123 and ending with nucleotide 1055 as shown in FIG. 2.

A second class of this third embodiment of the invention concerns a system for the transient expression of human neurokinin-1 receptor short form in a monkey kidney cell line (COS), the system comprising a vector comprising human neurokinin receptor short form (human NK1R sF) cDNA.

A third class of this third embodiment of the invention concerns a system for the expression of human neurokinin-1 receptor short form in a Chinese hamster ovarian cell line (CHO), the system comprising a vector comprising human neurokinin receptor short form (human NK1R sF) cDNA.

Within this class of the third embodiment is the sub-class wherein the expression system includes
A plasmid which comprises:
(a) a mammalian expression vector, such as pRcCMV, and
(b) a base sequence encoding human neurokinin-1 receptor short form protein.

Within this sub-class the neurokinin-1 receptor expression system comprises the nucleotide sequence of complementary DNA, beginning with nucleotide 123 and ending with nucleotide 1055 as shown in FIG. 2. It is understood, and is readily apparent to those skilled in the art that a wide variety of commonly used mammalian cell lines are suitable for use in the present invention. Suitable cell lines derived from mammalian species include, but are not limited to, cell lines of human, bovine, porcine, monkey, and rodent origin.

A fourth embodiment of the invention concerns a method of using any of the above expression systems for determining the binding affinity of a test sample for human neurokinin-1 receptor and/or NK1R sF.

In one class this embodiment concerns a method of using a Chinese hamster ovarian cell line (CHO), said line transplanted with a plasmid, which plasmid comprises:
(a) a mammalian expression vector, such as pRcCMV, and
(b) the base sequence encoding human neurokinin-1 receptor short form protein, the method which comprises:
  (1) expressing human neurokinin-1 receptor short form in said CHO cells;
  (2) addition of a test sample to a solution containing $^{125}$I-substance P and said cells;
  (3) incubating the products of Step (2), said incubation effective for expressing said the human neurokinin-1 receptor short form and effective for competitive binding of said $^{125}$I-substance P and said test sample to said human neurokinin-1 receptor short form;
  (4) separating said $^{125}$I-substance P which is bound to said human neurokinin-1 receptor short form from said $^{125}$I-substance P which is not bound;
  5) measuring the radioactivity of said $^{125}$I-substance P which is bound to said human neurokinin-1 receptor short form.

In a second class this embodiment concerns a method of using a monkey kidney cell line (COS), said line transplanted with a plasmid, which plasmid comprises:
(a) a mammalian expression vector, such as pCDM8, and
(b) the base sequence encoding human neurokinin-1 receptor short form protein, the method which comprises:
  (1) expressing human neurokinin-1 receptor short form in said COS cells;
  (2) addition of a test sample to a solution containing $^{125}$I-substance P and said cells;
  (3) incubating the products of Step (2), said incubation effective for expressing said the human neurokinin-1 receptor short form and effective for competitive binding of said $^{125}$I-substance P and said test sample to said human neurokinin-1 receptor short form;
  (4) separating said $^{125}$I-substance P which is bound to said human neurokinin-1 receptor short form from said $^{125}$I-substance P which is not bound;
  (5) measuring the radioactivity of said $^{125}$I-substance P which is bound to said human neurokinin-1 receptor short form.

In a third class this embodiment concerns a method of using a Chinese hamster ovarian cell line (CHO), said line transplanted with a plasmid which plasmid comprises
(a) a mammalian expression vector, such as pRcCMV, and
(b) the base sequence encoding human neurokinin-1 receptor short form protein, the method comprising:
  (1) expressing human neurokinin-1 receptor short form in said CHO cells;
  (2) equilibrating the product of Step (1) with $^3$H-myoinositol;
  (3) washing the product of Step (2);
  (4) incubating the product of Step (3) with a test sample in the presence of 10 mM LiCl, which results in the production of inositol monophosphate;
  (5) measuring the inositol monophosphate.

In overview, the present invention describes methods to isolate the human neurokinin-1 receptor short form (human NK1R sF) complementary DNA (cDNA) without prior knowledge of its protein sequence or gene sequence. Human NK1R and NFIR sF are membrane receptors for the neurotransmitter substance P. Polymerase chain reaction (PCR) technique was utilized for the isolation of human NK1R sF cDNA. In the approach, the regions of rat NK1R applicants thought to be similar to human NK1R were identified, oligonucleotide primers corresponding to those region were designed, PCR amplification was carried out to obtain part of the NK1R sF cDNA from human cells, and its DNA sequence was determined. The remaining part of the human NK1R sF cDNA was obtained from a human cDNA library utilizing the above sequence information of human NK1R sF cDNA.

The complete sequence of the human NK1R sF cDNA was determined, and its encoded protein sequence was deduced. Among other things, such sequence information is useful in the process of developing novel substance P antagonists.

Three heterologous expression systems were used to express the cloned human NK1R sF cDNA. The Xenopus oocyte expression enables one to determine the biological function of human NK1R sF The COS (a monkey kidney cell line) expression can be used to measure the ligand binding properties of human NK1R sF. The CHO (a Chinese hamster ovarian cell line) stable expression is suitable for natural product screen to identify potential therapeutic agent or other substances that bind to substance P receptor or human NK1R sF This cell line can also be used as an assay kit for determining the body fluid concentration of substance P in arthritis patients.

Assay protocols use the heterologously expressed human NK1R sF for determination of the binding affinity and antagonistic activity of substance P antagonists.

1) Isolation of human NK1R sF cDNA

As will be appreciated by those of skill in the art, NK1R has been believed to exist as a single type. Accordingly, a strategy was devised to isolate that single NK1R type. Surprisingly, the applicants unexpectedly found both a full length NK1R and a NK1R short form, the latter which is believed to constitute a previously unknown receptor sub-type.

To isolate the human NK1R cDNA in the absence of its sequence information, we developed methods to obtain three separate but overlapping cDNA clones in three steps. (i) We have adopted the homologous cloning strategy (Ohara et al., 1989, Proc. Nat. Acad. Sci., 86:5673–5677) to isolate cDNA clones encoding the central core region of human NK1R, with the assumption that the human NK1R sequence is similar to the published sequence (Yokota et al., 1989, J. Biol. Chem., 264:17649–17652) of rat NK1R in certain areas where appropriate PCR primers can be designed. Degenerate primers corresponding to the rat sequence were used in PCR amplification (Mullis and Faloona, 1987, Meth. Enzymol., 155:335) to obtain the cDNA encoding the central transmembrane core region of human NK1R from human mRNA. (ii) After determining the sequence of the core region in human NK1R, new primers corresponding to the human sequence were designed and a second homologous PCR amplification was performed using the human primer in the core region with degenerate primers corresponding to the N-terminal sequence of rat NK1R. The cDNA encoding the N-terminal region of human NK1R was thus obtained from human mRNA and its sequence was determined. (iii) An anchored PCR strategy was developed to isolate the cDNA encoding the C-terminal region of human NK1R, in which primers corresponding to the core region of human NK1R were used in combination with a primer corresponding to the sequence of a cloning vector to obtain the cDNA from a human cDNA library.

By use of this strategy, both NK1R and NK1R sF were isolated. To confirm the authenticity of the cDNA encoding human NK1R sF, an independent PCR amplification was performed to obtain the full length cDNA in a single step using primers from the 5' and 3' untranslated regions.

2) Expression of the cloned human NK1R sF

Three expression systems were developed for the cloned human NK1R sF. A transient expression in XenopuS oocytes resulted from microinjection of in vitro transcribed mRNA from the cloned cDNA (Xenopus Laevis from XENOPUS ONE, Ann Arbor, HI). This system allows the measurement of biological effect of NK1R sF activation upon ligand binding. Another transient expression in COS (a monkey kidney cell line, ATCC CRL 1651, ATCC Rockville, Md.) resulted from the transfection of the cloned cDNA under the control of vital promoter into mammalian cells (e.g., COS). The transfected cells are suitable for determination binding affinity of human NK1R sF for various ligands. Stable expression of human NK1R sF in mammalian cells (e.g., CHO, a Chinese hamster ovarian cell line, ATCC CRL 9096, ATCC Rockville, Md.) was achieved after integration of the transfected cDNA into the chromosomes of the host cells. These stable cell lines will constituently express the cloned human NK1R sF and can be propagated infinitely. Therefore, stable expression system is very useful in large scale drug screen, and can be used to determine substance p concentration in the biopsy sample of patients.

To establish a stable cell line expressing the cloned human NK1R sF, the cDNA was subcloned into the vector pRcCMV (INVITROGEN).

The electrophysiological assay of human NK1R sF expressed in Xenopus oocytes was based on the fact that NK1R activates the phospholipase C upon substance P binding, and phospholipase C in turn increases the intracellular calcium concentration through inositol tris-phosphate (IP$_3$) and IP$_3$-gated calcium channel on intracellular membranes. The calcium increase activates calcium-gated chloride channels on plasma membranes which gives rise to chloride current measurable by two electrode voltage clamp.

The binding assay of human NK1R sF expressed in COS or CHO is based on the use of $^{125}$I-substance P ($^{125}$I-SP, from DU PONT, Boston, Mass.) as a radioactively labeled ligand which competes with unlabeled substance P or any other ligand for binding to the human NK1R sF. Monolayer cell culture of COS or CHO was dissociated by the non-enzymatic solution (SPECIALTY MEDIA, Lavallette, N.J.) and resuspended in appropriate volume of the binding buffer (50 mM Tris pH 7.5, 5 hum MnCl$_2$, 150 mM NaCl, 0.04 mg/ml bacitracin, 0.004 mg/ml leupeptin, 0.2 mg/ml BSA, 0.01 mM phosphoramidon).

The activation of phospholipase C by NK1R sF can also be measured in CHO cells by determining the accumulation of inositol monophosphate which is a degradation product of IP$_3$.

In addition to large scale drug screening using the stable CHO cell line expressing the cloned human NK1R sF, other alternative applications will become apparent to those of skill in the art obvious. For example, the stable cell line can be used in the binding assay to determine the substance P concentration from biopsy samples. The human NK1R sF protein can also be injected into patients to reduce substance P concentration in some neurogenic inflammatory diseases.

The following examples are given for the purpose of illustrating the present invention and shall not be construed as being limitations on the scope or spirit of the present invention.

EXAMPLE 1

Step A

In the first step of obtaining the cDNA encoding the central core region of human NK1R sF, human mRNA was prepared from three human glioblastoma cell lines T98G, CCF-STTG1 and U87MG (obtained from the American Type Culture Collection, Rockville, Md.) by the FASTTRACK® method (INVITROGEN, San Diego, Calif.). Synthesis of first strand cDNA from 4 ug of human mRNA was initiated by oligo (dT) primers in a total volume of 20 ul according to protocols of the BRL cDNA synthesis system (BRL, LIFE TECHNOLOGIES, Inc., Gaithersburg, Md.). Ten ul of the first strand cDNA was used as template with three rat primers (50 pmol rspr2s4, 50 pmol rspr2s4h, and 100 pmol rspr7a2; see Table I for their sequences) in a primary PCR amplification in a total volume of 100 ul according to the GENEAMP® protocol (PERKIN ELMER CETUS, Norwalk, Conn.). Thirty cycles of PCR were performed using the following parameters: 1 min of denaturation at 94° C., 2 min of annealing at 40° C. and 4 min of extension at 72° C. with 2 sec of auto extension. Ten ul of the primary PCR product was used as template with the same primers in a secondary PCR amplification under the same cycling conditions to further amplify the DNA. Ten ul of the secondary PCR product was used as template with three rat primers (50 pmol rspr2s4, 50 pmol rspr2s4h, 50 pmol rspr7al and 50 pmol rspr7alh) in 30 cycles of tertiary PCR amplification with the following parameters: 1 min of denaturation at 94° C., 2 min of annealing at 45° C., and 4 min of extension at 72° C. with 2 sec of auto extension. The tertiary PCR product was analyzed by agarose gel electrophoresis and was found to contain a 600 bp DNA fragment. This DNA fragment was excised from the gel, purified by GENECLEAN® (Bio 101, La Jolla, Calif.), phosphorylated, and subcloned into Sma I site of the plasmid vector BLUESCRIPT SK+® (STRATAGENE, La Jolla, Calif.). The DNA sequence was determined by the Sequenase dideoxy chain termination method (USBC, Cleveland, Ohio). Sequence alignment analysis showed that this cDNA fragment is similar (90% identity at nucleotide level) to the central core region of rat NK1R from amino acid 91 to 280.

STEP B

After determination of the core region sequence of human NK1R sF, five antisense primers were synthesized based on the human sequence (hspr3a5, hspr5al, hspr5a2, hspr6al and hspr6a2; see Table II for their sequences). These primers would be used to obtain the N-terminal cDNA sequence of human NK1R sF. One of human glioblastoma mRNA and 6 uM of each of the above primers was used in first strand cDNA synthesis in a total volume of 20 ul according the BRL cDNA synthesis protocols. The cDNA was extracted by phenol-chloroform, precipitated by ethanol and dissolved in 30 ul of water. Ten ul of the cDNA was used as template with two rat primers (50 pmol rsprn and 50 pmol rsprnh> and one human primer (150 pmol hspr3a5> in the primary PCR amplification in a total volume of 100 ul. Thirty cycles were performed with the following parameters: 1 min denaturation at 94° C., 1 min of annealing at 55° C., and 3 min of extension at 72° C. Five ul of the primary PCR product was then used as template with two rat primers (50 pmol rsprn and 50 pmol rsprnh) and one human primer (100 pmol hspr3a4) in 30 cycles of secondary PCR amplification with the same parameters. Two ul of the secondary PCR product was used as template with two rat primers (50 pmol rsprn and 50 pmol rsprnh) and one human primer in 30 cycles of tertiary PCR amplification with the same parameters. The tertiary PCR product was analyzed by agarose gel electrophoresis and was found to contain a 500 bp fragment. This DNA fragment can hybridize with a human oligonucleotide (hspr3a2>, indicating it is not a non-specific by-product. This DNA fragment was excised from the gel, purified by GENECLEAN® (Bio 101), phosphorylated, and subcloned into Sma I site of the vector Bluescript SK+. DNA sequence analysis revealed that this fragment encodes the human NK1R sF N-terminal region and it also contains 5' untranslated sequence.

STEP C

In the third step, an anchored PCR protocol was developed in which the cDNA encoding the C-terminal region of human NK1R sF was obtained from a cDNA library using sense human primers and a primer corresponding to the vector sequence. Three ug of human glioblastoma mRNA was primed by 2.5 ug of oligo (dT) in the first strand cDNA synthesis in a total volume of 50 ul, followed by second strand cDNA synthesis according the BRL cDNA synthesis protocols. The cDNA product was then heated at 70° C. for 10 min. The yield of double stranded cDNA was determined by incorporating 1.25 uM of $^{32}$P-a-dCTP as tracer in the reaction. Four ul of T4 DNA polymerase was added to the reaction mixture and incubated at 37° C. for 10 min. The reaction was stopped by adding 16 ul of 250 mM EDTA, extracting with phenol/CHCl$_3$, and precipitating with ethanol. The cDNA was dissolved in 50 ul of BE buffer (10 mM HEPES-lmM EDTA). Small size cDNA was removed by the Select-D(RF) SPIN CO- LUMN ® (5'T03', Boulder, Colo.), and the large size eDNA was precipitated by ethanol and dissolved in 36 ul of water. Four ul of 0.2M Tris-10 mM spermidine-1 mM EDTA (pH7.5) was added to the tube and heated at 70° C. for 1 min. The cDNA was phosphorylated by adding 5 ul of blunt-end kinase buffer (0.5M Tris pH 9.5, 0.1M MSCl2, 50 mM DTT, 50% glycerol), 2.5 ul of 10 mM ATP, 2.5 ul of polynucleotide kinase, and incubating at 37° C. for 30 min. The cDNA was extracted by phenol/CHCl3, precipitated by ethanol and ligated to EcoRI linker according to the PROMEGA ECORI ® linker ligation protocol (PROMEGA, Madison, Wis.). Linker-ligated cDNA was then ligated to calf intestinal phosphatase-treated EcoRI site of the vector BLUESCRIPT SK+ ®. One ul of the ligated plasmid DNA was used as template in 30 cycles of primary PCR with two human primers (50 pmol hspr6s1 and 50 pmol hspr6s2) and 100 pmol of vector-specific primer t3 (obtained from STRATAGENE) with the following parameters: 1 min of denaturation at 94° C., 2 min of annealing at 55° C., and 4 min of extension at 72° C. with 2 sec auto extension. One ul of the primary PCR product was used in 30 cycles of secondary PCR amplification with one human primer (100 pmol hspr6s3) and the same vector-specific primer t3 under the same conditions. One ul of the secondary PCR product was used in 30 cycles of tertiary PCR amplification with one human primer (100 pmol hspr6s4) and 100 pmol of vector-specific primer SK (STRATAGENE) under the same conditions. A 400 bp DNA fragment was detected which also hybridized to a human oligo probe hspr6s5. This DNA fragment was excised from the agarose gel, purified by GENECLEAN ® (BIO 101), phosphorylated, and subcloned into Sma 1 site of the vector BLUESCRIPT. SK+ ®. DNA sequence analysis revealed that it encodes the C-terminal region of human NK1R sF amd contains 3' untranslated sequence.

STEP D

Since three separate but overlapping cDNA clones encoding human NK1R sF were isolated above and the possibility of alternative pre-mRNA splicing exists, it is necessary to confirm the authenticity of the full length cDNA sequence by isolating a full length cDNA directly. Based on the above sequence in the untranslated region, primers were synthesized which should give rise to a full length cDNA. Using the PERKIN ELMER CETUS RNA PCR amplification kit (Perkin Elmer Cetus), cDNA was synthesized from 1.5 ug of human glioblastoma mRNA in a total volume of 20 ul with 50 pmol of the human primer hspr12utal. One half of the first strand cDNA was used as template in 30 cycles of primary PCR amplification with two human primers (50 pmol hspr12utal, 50 pmol hspr5uts1) with the following parameters: 1 min of denaturation at 94° C., 2 min of annealing at 55° C., and 4 min of extension at 55° C. with 2 sec auto extension. Ten ul of the primary PCR product was used as template in 30 cycles of secondary PCR amplification with two human primers (50 pmol hspr12uta2 and 50 pmol hspr5uts2) under the same conditions. A 1100 bp DNA fragment was excised from agarose gel, purified by GENECLEAN ® (BIO 101), digested with restriction endonucleases with EcoRI and Not I, and subcloned into the vector BLUESCRIPT SK+ ®. DNA sequence analysis confirmed the general structure of the cloned human NK1R cDNA sF. The sequence of human NK1R sF cDNA is shown in FIG. 2.

TABLE I

Primers based on rat NK1R sequence. The last letter "h" in some primers denotes that human codon bias was incorporated (Lathe, 1985, J. Mol. Biol. 183:1–12). The position number in the rat cDNA sequence was defined by Yokota et al. (J. Biol. Chem., 1989, 264:17649–17652).

| Name | Sequence (SEQ ID NO:__:) | Position | Direction |
|---|---|---|---|
| rspr2s4 | TGCATGGCTGCATTCAAT (2) | 238–255 | sense |
| rspr2s4h | TGCATGGCTGCCTTCAA (3) | 238–254 | sense |
| rspr7a2 | ACAGTAGATGATGGGGTTGTACAT (4) | 918–894 | antisense |
| rspr7a1 | CAGGTAGACCTGCTGGATGAACTT (5) | 864–941 | antisense |
| rspr7a1h | CAGGTACACCTGCTGGATGAACTT (6) | 864–941 | antisense |
| rsprn | ATGGATAACGTCCTTCCTAT (7) | 1–20 | sense |
| rsprnh | ATGGACAATGTGCTGCCCA (8) | 1–19 | sense |

TABLE II

Primers based on the human NK1R cDNA sF sequence. Position number is defined in the sequence listing in the text. The nucleotides in parentheses are not present in the human NK1R sF cDNA; they are restriction sites for subcloning purpose.

| Name | Sequence(SEQ ID NO:__:) | Position | Direction |
|---|---|---|---|
| hspr3a2 | GAAGAAGTTGTGGAACTTGCA (9) | 455–435 | antisense |
| hspr3a1 | CATGGAGTAGATACTGGCGAA (10) | 491–471 | antisense |
| hspr3a4 | GGATGTATGATGGCCATGTA (11) | 532–513 | antisense |
| hspr3a5 | ACTTTGGTGGCTGTGGCTGA (12) | 568–549 | antisense |
| hspr5a1 | ATGCATAGCCAATCACCAGCA (13) | 768–748 | antisense |
| hspr5a2 | CATAGTGTGATTCCCACTAC (14) | 793–774 | antisense |
| hspr6a1 | TGCACACCACGACAATCATCA (15) | 888–868 | antisense |
| hspr6a2 | TTGATGTAGGGCAGGAGGAA (16) | 943–924 | antisense |
| hspr6s1 | GCAAGTCTCTGCCAAGCGCAA (17) | 836–856 | sense |
| hspr6s2 | TGATGATTGTCGTGGTGTGCA (18) | 868–888 | sense |
| hspr6s3 | TTCCACATCTTCTTCCTCCT (19) | 912–931 | sense |
| hspr6s4 | CTACATCAACCCAGATCTCT (20) | 935–954 | sense |
| hspr6s5 | TCTCTACCTGAAGAAGTT (21) | 950–967 | sense |
| hspr12uta1 | TCACAGCTGGGTTTACTCAT (22) | 1050–1131 | antisense |
| hspr12uta2 | (GACATGCGGCCGC)CGCTTGGCCACTGTGTAT (23) | 1121–1104 | antisense |

TABLE II-continued

Primers based on the human NK1R cDNA sF sequence. Position number is defined in the sequence listing in the text. The nucleotides in parentheses are not present in the human NK1R sF cDNA; they are restriction sites for subcloning purpose.

| Name | Sequence(SEQ ID NO:__:) | Position | Direction |
|---|---|---|---|
| hspr5uts1 | CCTCCTGTCTGGCTTTAGAA (24) | 16–35 | sense |
| hspr5uts2 | (GCGCAGAATTC)GTGTACAGATAGTAGGCTT (25) | 86–105 | senset |

EXAMPLE 2

Expression in Xenopus Oocytes

To express the human NKIR sF cDNA in Xenopus oocytes, the cDNA was cloned into an in vitro transcription vector BLUESCRIPT SK+ ® (STRATAGENE) which contains the T7 promoter for initiation of T7 RNA polymerase catalyzed RNA synthesis. One ug of linear plasmid DNA which contained the human NK1R cDNA downstream of the T7 promoter was used in the in vitro transcription reaction containing 40 mM Tris pH 7.5, 50 mM NaCl, 8 mM $MgCl_2$, 2 mM spermidine, 0.4 mM CTP, 0.4 mM ATP, 0.4 mM GTP, 0.16 mM GTP, 2.5 ul CAP analog (STRATAGENE), 30 mM DTT, 1 U RNase Block II (STRATAGENE), 0.83 pmol $^{32}$P-a-CTP and 25 U of T7 RNA polymerase. The reaction tube was incubated at 37° C. for 1 hour. Usually 5 ug of RNA was synthesized as quantitated by incorporation of $^{32}$P-a-CTP into RNA. After RNA synthesis, the plasmid DNA was removed by adding 10 U of RNase free DNase and 1U of RNase Block II. The reaction mixture was extracted by phenol/$CHCl_3$, and the unincorporated nucleotides were removed by the Select-D(RF) spin column (5'TO3'). The RNA transcript was precipitated by ethanol twice and dissolved in RNase free water. Oocytes were removed from Xenopus frogs, treated with 2 mg/ml collagenase (specific activity<0.3 U/mg, BOEHRINGERMANNHEIM, Indianapolis, Ind.) in OR-2 buffer (82.5 mM NaCl, 2 mMKCl, 1 mMMgCl2, 5 mM HEPES, pH 7.4) for 4 hours at 19° C. The dissociated oocytes were incubated in 0R-2 buffer supplemented by 1.8 mM $CaCl_2$, 0.5 mg/ml gentamycin and 0.5 mH theophylline at 19° C. overnight before injection. A 50 nl aliquot contain 2 ng of RNA transcript was injected into each oocyte. The injected oocytes were incubated at 19° C. for 2 days before electrophysiological recording (see Example 3 for assay method).

Expression in COS

To express the human NK1R sF transiently in COS, the cDNA was cloned into the expression vector pCDM9 which was derived from pCDM8 (INVITROGEN) by inserting the ampicillin resistance gene (nucleotide 1973 to 2964 from BLUESCRIPT SK+ ®) into the Sac II site. Transfection of 20 ug of the plasmid DNA into 10 millions COS cells was achieved by electropotation in 800 ul of transfection buffer (135 mMNaCl, 1.2 mM $CaCl_2$, 1.2 mMMgCl2, 2.4 mMK2HPO4, 0.6 mM $KH_2PO_4$, 10 mM glucose, 10 mM HEPES pH 7.4) at 260 V and 950 uF using the IBI GENEZAPPER ®(IBI, New Haven, Conn.). The cells were incubated in 10% fetal calf serum, 2 mM glutamine, .100U/ml penicillin-streptomycin, and 90% DMEM media (GIBC0, Grand Island, N.Y.) in 5% $CO_2$ at 37° C. for three days before the binding assay.

Stable Expression in CHO

To establish a stable cell line expressing the cloned human NK1R sF, the cDNA is subcloned into the vector pRcCMV (INVITROGEN). Transfection of 20 ug of the plasmid DNA into CII0 cells is achieved by electropotation in 800 ul of transfection buffer supplement with 0.625 mg/ml liefring sperm DNA at 300 V and 950 uF using the IBI GENEZAPPER ® (IBI). The transfected cells are incubated in CHO media [10% fetal calf serum, 100 U/ml penicilin-streptomycin, 2 mM glutamine, 1/500 hypoxanthine-thymidine (ATCC ) , 90% IMDM media (JRH BIOSCIENCES, Lenexa, Kans.) , 0.7 mg/ml G418 (GIBC0>] in 5% $CO_2$ at 37° C. until colonies are visible. Each colony was separated and propagated. The cell clone with the highest number of human NK1R is selected for subsequent application in the assay of Example 3.

EXAMPLE 3

Assay Protocol Using Oocytes

Figure 4:
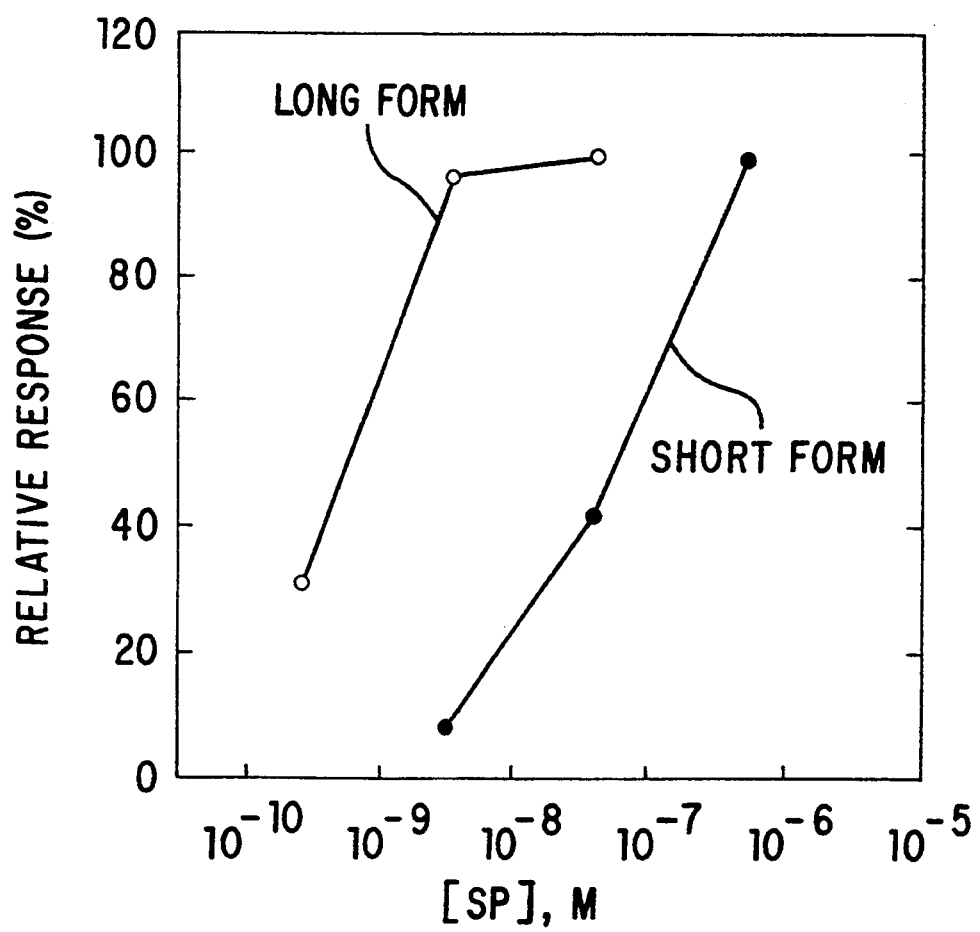
FIG. 4: Activating phospholipase C as mediated by neurokinin-1 receptor short and long forms.

The oocyte was voltage-clamped at −80 mV by the model 8500 intracellular preamp-clamp (DAGAN, Minneapolis, Minn.). The recoding chamber was continuously perfused with recording buffer (96 mM NaCl, 2 mMKCl, 1.8 mM $CaCl_2$, 5 mMHEPES, pH 7.4). Chloride current was elicited by applying substance P (from 0.1 nM to 1000 nM) to the recording chamber. At least three oocytes were measured for each concentration. The antagonistic activity of any potential substance P antagonist can be assessed by determining the inhibition of substance P response. Likewise, NK1R and NK1R sF agonists can be identified by their ability to stimulate a response in oocytes injected with NK1R sF mRNA but not in uninjected oocytes. As shown in FIG. 4, the activation of phospholipase C mediated by the short and long forms of NK1R also exhibit a differential sensitivity to the agonist substance P.

Assay Protocol Using COS or CHO

The binding assay of human NK1R sF expressed in COS (or CHO) is based on the use of $^{125}$I-substance P ($^{125}$I-SP, from DU PONT, Boston, Mass.) as a radioactively labeled ligand. Monolayer cell culture of COS (or CHO) was dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 1000 cpm of specific $^{125}$I-Sp binding at 6.7 riM. In the binding assay, 200 ul of cells were added to a tube containing 20 ul binding buffer and 200 ul of various serial dilution of $^{125}$I-SP stock solution. The $^{125}$I-SP stock solution was at 14 nM with a specific activity of 40 cpm/fmol. The non-specific binding was determined by including 20 ul of 210 uM unlabeled SP instead of buffer in the above assay mixture. The mixture was incubated at 4° C. for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mMMnCl$_2$, 150 mM NaCl) three times and its radioactivity was determined by gamma counter. Illustrative of this method of using these expression systems are the results shown in FIG. 3. These results show the difference in binding affinity of substance P for the short and long forms of human NK1R.

ALTERNATIVE PROTOCOL

The activation of phospholipase C by NK1R sF may also be measured in CHO cells by determining the accumulation of inositol monophosphate which is a degradation product of IP$_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without antagonist, and continued incubation at 37° C. for 15 min. Substance P is added to the well at final concentration of 0.3 nM to activate the human NK1R sF. After 30 min of incubation at 37° C., the media is removed and 0.1N HCl is added. Each well is sonicated at 4° C. and extracted with CHCl$_3$/methanol (1:1). The aqueous phase is applied to a 1 ml Dowex AG 1X8 ion exchange column. The column is washed with 0.1N formic acid followed by 0.025M ammonium formate-0.1 N formic acid. The inositol monophosphate is eluted with 0.2M ammonium formate-0.1N formic acid and quantitated by beta counter.

While the foregoing specification teaches the principles of the present invention, with examples provided for the purpose of illustration, it will be understood that the practice of the invention encompasses all of the casual variations, adaptioations, modifications, deletions, or additions of procedures and protocols described herein, as come within the scope of the following claims and its equivalents.

---

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:1:

```
GAAAAAGCCT  TCCACCCTCC  TGTCTGGCTT  TAGAAGGACC  CTGAGCCCCA  GGCGCCACGA        60

CAGGACTCTG  CTGCAGAGGG  GGGTTGTGTA  CAGATAGTAG  GGCTTACCG   CCTAGCTTCG       120

AA                                                                          122
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:2:

```
TGCATGGCTG  CATTCAAT                                                         18
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:3:

TGCATGGCTG CCTTCAA 17

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:4:

ACAGTAGATG ATGGGGTTGT ACAT 24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:5:

CAGGTAGACC TGCTGGATGA ACTT 24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:6:

CAGGTACACC TGCTGGATGA ACTT 24

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:7:

ATGGATAACG TCCTTCCTAT 20

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:8:

ATGGACAATG TGCTGCCCA 19

( 2 ) INFORMATION FOR SEQ ID NO:9:

( i ) SEQUENCE CHARACTERISTICS:
        ( A ) LENGTH: 21 base pairs ( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:9:

GAAGAAGTTG TGGAACTTGC A 21

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:10:

CATGGAGTAG ATACTGGCGA A 21

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:11:

GGATGTATGA TGGCCATGTA 20

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:12:

ACTTTGGTGG CTGTGGCTGA 20

( 2 ) INFORMATION FOR SEQ ID NO:13:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:13:

ATGCATAGCC AATCACCAGC A 21

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE:

( x i ) SEQUENCE DESCRIPTION: SEQ ID NO:14:

CATAGTGTGA TTCCCACTAC                                                                    20

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:15:

TGCACACCAC GACAATCATC A                                                                  21

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:16:

TTGATGTAGG GCAGGAGGAA                                                                    20

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:17:

GCAAGTCTCT GCCAAGCGCA A                                                                  21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:18:

TGATGATTGT CGTGGTGTGC A                                                                  21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:19:

TTCCACATCT TCTTCCTCCT                                                                    20

(2) INFORMATION FOR SEQ ID NO:20:

(i) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:20:

CTACATCAAC CCAGATCTCT  20

(2) INFORMATION FOR SEQ ID NO:21:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:21:

TCTCTACCTG AAGAAGTT  18

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:22:

TCACAGCTGG GTTTACTCAT  20

(2) INFORMATION FOR SEQ ID NO:23:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:23:

CGCTTGGCCA CTGTGTAT  18

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:24:

CCTCCTGTCT GGCTTTAGAA  20

(2) INFORMATION FOR SEQ ID NO:25:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE:

( x i ) SEQUENCE DESCRIPTION: SEQ ID NO:25:

GTGTACAGAT AGTAGGCTT 19

( 2 ) INFORMATION FOR SEQ ID NO:26:

( i ) SEQUENCE CHARACTERISTICS:
      ( A ) LENGTH: 311 amino acids
      ( B ) TYPE: amino acid
      ( C ) STRANDEDNESS: single
      ( D ) TOPOLOGY: linear ( i i ) MOLECULE TYPE:

( x i ) SEQUENCE DESCRIPTION: SEQ ID NO:26:

| | | | | | | | | | | | | | | |
|---|---|---|---|---|---|---|---|---|---|---|---|---|---|---|
| Met<br>1 | Asp | Asn | Val | Leu<br>5 | Pro | Val | Asp | Ser | Asp<br>10 | Leu | Ser | Pro | Asn | Ile<br>15 | Ser |
| Thr | Asn | Thr | Ser<br>20 | Glu | Pro | Asn | Gln | Phe<br>25 | Val | Gln | Pro | Ala | Trp<br>30 | Gln | Ile |
| Val | Leu | Trp<br>35 | Ala | Ala | Ala | Tyr | Thr<br>40 | Val | Ile | Val | Val | Thr<br>45 | Ser | Val | Val |
| Gly | Asn<br>50 | Val | Val | Val | Met | Trp<br>55 | Ile | Ile | Leu | Ala | His<br>60 | Lys | Arg | Met | Arg |
| Thr<br>65 | Val | Thr | Asn | Tyr | Phe<br>70 | Leu | Val | Asn | Leu | Ala<br>75 | Phe | Ala | Glu | Ala | Ser<br>80 |
| Met | Ala | Ala | Phe | Asn<br>85 | Thr | Val | Val | Asn | Phe<br>90 | Thr | Tyr | Ala | Val | His<br>95 | Asn |
| Glu | Trp | Tyr | Tyr<br>100 | Gly | Leu | Phe | Tyr | Cys<br>105 | Lys | Phe | His | Asn | Phe<br>110 | Phe | Pro |
| Ile | Ala | Ala<br>115 | Val | Phe | Ala | Ser | Ile<br>120 | Tyr | Ser | Met | Thr | Ala<br>125 | Val | Ala | Phe |
| Asp | Arg<br>130 | Tyr | Met | Ala | Ile | Ile<br>135 | His | Pro | Leu | Gln | Pro<br>140 | Arg | Leu | Ser | Ala |
| Thr<br>145 | Ala | Thr | Lys | Val | Val<br>150 | Ile | Cys | Val | Ile | Trp<br>155 | Val | Leu | Ala | Leu | Leu<br>160 |
| Leu | Ala | Phe | Pro | Gln<br>165 | Gly | Tyr | Tyr | Ser | Thr<br>170 | Thr | Glu | Thr | Met | Pro<br>175 | Ser |
| Arg | Val | Val | Cys<br>180 | Met | Ile | Glu | Trp | Pro<br>185 | Glu | His | Pro | Asn | Lys<br>190 | Ile | Tyr |
| Glu | Lys | Val<br>195 | Tyr | His | Ile | Cys | Val<br>200 | Thr | Val | Leu | Ile | Tyr<br>205 | Phe | Leu | Pro |
| Leu | Leu<br>210 | Val | Ile | Gly | Tyr | Ala<br>215 | Tyr | Thr | Val | Val | Gly<br>220 | Ile | Thr | Leu | Trp |
| Ala<br>225 | Ser | Glu | Ile | Pro | Gly<br>230 | Asp | Ser | Ser | Asp | Arg<br>235 | Tyr | His | Glu | Gln | Val<br>240 |
| Ser | Ala | Lys | Arg | Lys<br>245 | Val | Val | Lys | Met | Met<br>250 | Ile | Val | Val | Val | Cys<br>255 | Thr |
| Phe | Ala | Ile | Cys<br>260 | Trp | Leu | Pro | Phe | His<br>265 | Ile | Phe | Phe | Leu | Leu<br>270 | Pro | Tyr |
| Ile | Asn | Pro | Asp<br>275 | Leu | Tyr | Leu | Lys | Lys<br>280 | Phe | Ile | Gln | Gln<br>285 | Val | Tyr | Leu |
| Ala | Ile<br>290 | Met | Trp | Leu | Ala | Met<br>295 | Ser | Ser | Thr | Met | Tyr<br>300 | Asn | Pro | Ile | Ile |
| Tyr<br>305 | Cys | Cys | Leu | Asn | Asp<br>310 | Arg | | | | | | | | | |

( 2 ) INFORMATION FOR SEQ ID NO:27:

( i ) SEQUENCE CHARACTERISTICS:
      ( A ) LENGTH: 1269 base pairs (B) TYPE: nucleic acid
(C) STRANDEDNESS: single
(D) TOPOLOGY: linear (ii) MOLECULE TYPE:

(xi) SEQUENCE DESCRIPTION: SEQ ID NO:27:

```
GAAAAAGCCT TCCACCCTCC TGTCTGGCTT TAGAAGGACC CTGAGCCCCA GGCGCCACGA      60
CAGGACTCTG CTGCAGAGGG GGGTTGTGTA CAGATAGTAG GGCTTTACCG CCTAGCTTCG     120
AAATGGATAA CGTCCTCCCG GTGGACTCAG ACCTCTCCCC AAACATCTCC ACTAACACCT     180
CGGAACCCAA TCAGTTCGTG CAACCAGCCT GGCAAATTGT CCTTTGGGCA GCTGCCTACA     240
CGGTCATTGT GGTGACCTCT GTGGTGGGCA ACGTGGTAGT GATGTGGATC ATCTTAGCCC     300
ACAAAAGAAT GAGGACAGTG ACGAACTATT TTCTGGTGAA CCTGGCCTTC GCGGAGGCCT     360
CCATGGCTGC ATTCAATACA GTGGTGAACT TCACCTATGC TGTCCACAAC GAATGGTACT     420
ACGGCCTGTT CTACTGCAAG TTCCACAACT TCTTCCCCAT CGCCGCTGTC TTCGCCAGTA     480
TCTACTCCAT GACGGCTGTG GCCTTTGATA GGTACATGGC CATCATACAT CCCCTCCAGC     540
CCCGGCTGTC AGCCACAGCC ACCAAAGTGG TCATCTGTGT CATCTGGGTC CTGGCTCTCC     600
TGCTGGCCTT CCCCCAGGGC TACTACTCAA CCACAGAGAC CATGCCCAGC AGAGTCGTGT     660
GCATGATCGA ATGGCCAGAG CATCCGAACA AGATTTATGA AAAGTGTAC CACATCTGTG      720
TGACTGTGCT GATCTACTTC CTCCCCCTGC TGGTGATTGG CTATGCATAC ACCGTAGTGG     780
GAATCACACT ATGGGCCAGT GAGATCCCCG GGACTCCTC TGACCGCTAC CACGAGCAAG      840
TCTCTGCCAA GCGCAAGGTG GTCAAAATGA TGATTGTCGT GGTGTGCACC TTCGCCATCT     900
GCTGGCTGCC CTTCCACATC TTCTTCCTCC TGCCCTACAT CAACCCAGAT CTCTACCTGA     960
AGAAGTTTAT CCAGCAGGTC TACCTGGCCA TCATGTGGCT GGCCATGAGC TCCACCATGT    1020
ACAACCCCAT CATCTACTGC TGCCTCAATG ACAGGTGAGG ATCCCAACCC CATGAGCTCT    1080
CCAGGGGCCA CAAGACCATC TACATACACA GTGGCCAAGC GGCATCCTAA ATGAGTAAAC    1140
CCAGCTGTGA GACAAGAGGG ACAAGTGGGG ACTGCAGCTA ACTTATCATC ACACAACTCA    1200
GCCTGGCTGA TTATCACCAT CCAGGAATGG GAGCCCGGAG TAGACTGATT TTCTTTTTTT    1260
CTTTTCCAC                                                            1269
```

What is claimed is:

1. A method of determining the binding of a test sample to human neurokinin-1 receptor short form the human neurokinin-1 receptor short form having the amino acid sequence (SEQ ID:26:)

| Met | Asp | Asn | Val | Leu | Pro | Val | Asp | Ser |
| 1 | | | | 5 | | | | |
| | | Asp | Leu | Ser | Pro | Asn | Ile | Ser |
| | | 10 | | | | | 15 | |
| Thr | Asn | Thr | Ser | Glu | Pro | Asn | Gln | Phe |
| | | | 20 | | | | | 25 |
| | | Val | Gln | Pro | Ala | Trp | Gln | Ile |
| | | | | | | 30 | | |
| Val | Leu | Trp | Ala | Ala | Ala | Tyr | Thr | Val |
| | | 35 | | | | | 40 | |
| | | Ile | Val | Val | Thr | Ser | Val | Val |
| | | | | | 45 | | | |
| Gly | Asn | Val | Val | Val | Met | Trp | Ile | Ile |
| | 50 | | | | | 55 | | |
| | | Leu | Ala | His | Lys | Arg | Met | Arg |
| | | | | 60 | | | | |
| Thr | Val | Thr | Asn | Tyr | Phe | Leu | Val | Asn |
| 65 | | | | | 70 | | | |
| | | Leu | Ala | Phe | Ala | Glu | Ala | Ser |
| | | | 75 | | | | | 80 |
| Met | Ala | Ala | Phe | Asn | Thr | Val | Val | Asn |
| | | | | 85 | | | | |
| | | Phe | Thr | Tyr | Ala | Val | His | Asn |
| | | 90 | | | | | 95 | |
| Glu | Trp | Tyr | Tyr | Gly | Leu | Phe | Tyr | Cys |
| | | | 100 | | | | | 105 |
| | | Lys | Phe | His | Asn | Phe | Phe | Pro |
| | | | | | | 110 | | |
| Ile | Ala | Ala | Val | Phe | Ala | Ser | Ile | Tyr |
| | | 115 | | | | | 120 | |
| | | Ser | Met | Thr | Ala | Val | Ala | Phe |
| | | | | | 125 | | | |
| Asp | Arg | Tyr | Met | Ala | Ile | Ile | His | Pro |
| | 130 | | | | | 135 | | |
| | | Leu | Gln | Pro | Arg | Leu | Ser | Ala |
| | | | | 140 | | | | |
| Thr | Ala | Thr | Lys | Val | Val | Ile | Cys | Val |
| 145 | | | | | 150 | | | |

-continued

| | | | | | | |
|---|---|---|---|---|---|---|
| Ile | Trp 155 | Val | Leu | Ala | Leu | Leu 160 |
| Leu | Ala | Phe | Pro | Gln 165 | Gly | Tyr Tyr Ser |
| | Thr 170 | Thr | Glu | Thr | Met | Pro Ser 175 |
| Arg | Val | Val | Cys 180 | Met | Ile | Glu Trp Pro 185 |
| | Glu | His | Pro | Asn | Lys 190 | Ile Tyr |
| Glu | Lys | Val 195 | Tyr | His | Ile | Cys Val Thr 200 |
| | Val | Leu | Ile | Tyr 205 | Phe | Leu Pro |
| Leu | Leu 210 | Val | Ile | Gly | Tyr | Ala Tyr Thr 215 |
| | Val | Val | Gly 220 | Ile | Thr | Leu Trp |
| Ala 225 | Ser | Glu | Ile | Pro | Gly 230 | Asp Ser Ser |
| | Asp | Arg 235 | Tyr | His | Glu | Gln Val 240 |
| Ser | Ala | Lys | Arg | Lys 245 | Val | Val Lys Met |
| | Met 250 | Ile | Val | Val | Val | Cys Thr 255 |
| Phe | Ala | Ile | Cys 260 | Trp | Leu | Pro Phe His 265 |
| | Ile | Phe | Phe | Leu 270 | Leu | Pro Tyr |
| Ile | Asn | Pro 275 | Asp | Leu | Tyr | Leu Lys Lys 280 |
| | Phe | Ile | Gln | Gln 285 | Val | Tyr Leu |
| Ala | Ile 290 | Met | Trp | Leu | Ala | Met Ser Ser 295 |
| | Thr | Met | Tyr 300 | Asn | Pro | Ile Ile |
| Tyr 305 | Cys | Cys | Leu | Asn | Asp 310 | Arg |

, expressed by a Chinese hamster ovarian cell line, the cell line comprising a mammalian expression system encoding human neurokinin-1 receptor short form, the method comprising:

(a) adding a test sample to a solution containing $^{125}$I-substance P;

(b) incubating the solution of step (a) with cells from the cell line:

(c) separating the $^{125}$I-substance P which is not bound to the human neurokinin-1 receptor short form from the $^{125}$I-substance P which is bound;

(d) determining the amount of the $^{125}$I-substance P which is bound to the human neurokinin-1 receptor short form; and (e) comparing the amount of $^{125}$I-substance P which is bound to the human neurokinin-1 receptor short form in the presence of test sample to the amount which is bound in the absence of the test sample as an indication of the binding of the test sample to human neurokinin-1 receptor short form.

2. The method of claim 1 wherein the mammalian expression system contains the cytomegalovirus promoter.

3. A method of determining the binding of a test sample to human neurokinin-1 receptor short form the human neurokinin-1 receptor short form having the amino acid sequence (SEQ ID NO:26:)

| | | | | | | |
|---|---|---|---|---|---|---|
| Met 1 | Asp | Asn | Val | Leu 5 | Pro | Val Asp Ser |
| | Asp 10 | Leu | Ser | Pro | Asn | Ile Ser 15 |
| Thr | Asn | Thr | Ser 20 | Glu | Pro | Asn Gln Phe 25 |
| | Val | Gln | Pro | Ala | Trp 30 | Gln Ile |
| Val | Leu | Trp 35 | Ala | Ala | Ala | Tyr Thr Val 40 |
| | Ile | Val | Val | Thr | Ser 45 | Val Val |
| Gly | Asn 50 | Val | Val | Val | Met | Trp Ile Ile 55 |
| | Leu | Ala | His | Lys 60 | Arg | Met Arg |
| Thr 65 | Val | Thr | Asn | Tyr | Phe 70 | Leu Val Asn |
| | Leu | Ala 75 | Phe | Ala | Glu | Ala Ser 80 |
| Met | Ala | Ala | Phe | Asn 85 | Thr | Val Val Asn |
| | Phe 90 | Thr | Tyr | Ala | Val | His Asn 95 |
| Glu | Trp | Tyr | Tyr 100 | Gly | Leu | Phe Tyr Cys 105 |
| | Lys | Phe | His | Asn | Phe 110 | Phe Pro |
| Ile | Ala | Ala 115 | Val | Phe | Ala | Ser Ile Tyr 120 |
| | Ser | Met | Thr | Ala 125 | Val | Ala Phe |
| Asp | Arg 130 | Tyr | Met | Ala | Ile | Ile His Pro 135 |
| | Leu | Gln | Pro | Arg | Leu 140 | Ser Ala |
| Thr 145 | Ala | Thr | Lys | Val | Val 150 | Ile Cys Val |
| | Ile | Trp 155 | Val | Leu | Ala | Leu Leu 160 |
| Leu | Ala | Phe | Pro | Gln 165 | Gly | Tyr Tyr Ser |
| | Thr 170 | Thr | Glu | Thr | Met | Pro Ser 175 |
| Arg | Val | Val | Cys 180 | Met | Ile | Glu Trp Pro 185 |
| | Glu | His | Pro | Asn | Lys 190 | Ile Tyr |
| Glu | Lys | Val 195 | Tyr | His | Ile | Cys Val Thr 200 |
| | Val | Leu | Ile | Tyr 205 | Phe | Leu Pro |
| Leu | Leu 210 | Val | Ile | Gly | Tyr | Ala Tyr Thr 215 |
| | Val | Val | Gly 220 | Ile | Thr | Leu Trp |
| Ala 225 | Ser | Glu | Ile | Pro | Gly 230 | Asp Ser Ser |
| | Asp | Arg 235 | Tyr | His | Glu | Gln Val 240 |
| Ser | Ala | Lys | Arg | Lys 245 | Val | Val Lys Met |
| | Met 250 | Ile | Val | Val | Val | Cys Thr 255 |

-continued

```
Phe  Ala  Ile  Cys  Trp  Leu  Pro  Phe  His
              260                      265
                   Ile  Phe  Phe  Leu  Leu  Pro  Tyr
                                  270

Ile  Asn  Pro  Asp  Leu  Tyr  Leu  Lys  Lys
          275                      280
                   Phe  Ile  Gln  Gln  Val  Tyr  Leu
                            285

Ala  Ile  Met  Trp  Leu  Ala  Met  Ser  Ser
          290                      295
                   Thr  Met  Tyr  Asn  Pro  Ile  Ile
                            300

Tyr  Cys  Cys  Leu  Asn  Asp  Arg
305                      310          ,
``` expressed by a Chinese hamster ovarian cell line, the cell line comprising a mammalian expression system encoding human neurokinin-1 receptor short form, the method comprising:

(a) equilibrating cells from the cell line with $^3$H-myoinositol;
(b) washing the product of step (a);
(c) incubating the product of step (b) in the presence of a test sample and in the presence of 10 mM LiCl which results in the production of $^3$H-inositol monophosphate;
(d) determining the amount of $^3$H-inositol monophosphate; and
(e) comparing the amount of $^3$H-inositol monophosphate which is produced in the presence of test sample to the amount of $^3$H-inositol monophosphate which is produced in the absence of the test sample as an indication of the binding of the test sample to human neurokinin-1 receptor short form.

4. The method of claim 3 wherein the mammalian expression system contains the cytomegalovirus promoter.

* * * * *